United States Patent [19]
Skiba et al.

[11] Patent Number: 5,149,506
[45] Date of Patent: Sep. 22, 1992

[54] STOOL COLLECTION AND TRANSPORT DEVICE

[75] Inventors: Barbara T. Skiba, Chicago; Donald R. Harreld, Woodstock; Lawrence G. Ponsi, Wheeling, all of Ill.

[73] Assignee: Sage Products, Inc., Crystal Lake, Ill.

[21] Appl. No.: 743,023

[22] Filed: Aug. 9, 1991

[51] Int. Cl.5 .............................. G01N 1/00
[52] U.S. Cl. ........................ 422/102; 422/61; 422/58; 209/17; 73/864.41; 128/757
[58] Field of Search ........... 422/102, 58, 61, 99; 209/17; 73/864.41; 128/304, 305, 757

[56] References Cited

U.S. PATENT DOCUMENTS

| | | | |
|---|---|---|---|
| 4,304,139 | 12/1981 | Johnson | 73/864.41 |
| 4,559,837 | 12/1985 | Cerqueira | 422/102 |
| 4,678,559 | 7/1987 | Szabados | 209/17 |
| 4,735,905 | 4/1988 | Parker | 422/102 |
| 4,753,358 | 6/1988 | Virca et al. | 215/230 |
| 4,849,173 | 7/1989 | Chang | 422/102 |
| 4,956,298 | 9/1990 | Diekmann | 435/287 |

*Primary Examiner*—Lynn M. Kummert
*Attorney, Agent, or Firm*—Lee, Mann, Smith, McWilliams, Sweeney & Ohlson

[57] ABSTRACT

A device for collection and transporting of stool samples. The device has a container with a lid having a spoon secured to the underside of the lid. The spoon is angled at approximately 45° to facilitate sample collection, and has a generally straight cutting edge. A secondary access aperture is provided in the lid for accessing the interior of the container once the lid has been applied.

6 Claims, 1 Drawing Sheet

STOOL COLLECTION AND TRANSPORT DEVICE

BACKGROUND OF THE INVENTION

This invention relates to collection of stool samples, and in particular to a device for collection and transport of stool samples which promotes ease of stool collection and ease of access to the interior of the collection container once a sample has been collected.

Stool sampling is an important facet of medical care. Typically, samples are gathered with a stick or a spatula, and then placed in a container. If a portion of the sample is to be tested, the entire lid of the container is removed and another stick or spatula or similar means is used to remove the desired stool portion.

Such collection methods are awkward, at best, and susceptible to both contamination of the sample and contamination of the person collecting the sample. Use of a separate stick or spatula requires cleaning or disposal of a separate, contaminated element. Also, loose or liquid samples are practically impossible to properly collect with a stick or spatula.

SUMMARY OF THE INVENTION

The invention provides a compact, versatile stool collection and transport device which has an upright container having an open mouth at the top thereof. A removable lid is provided for the container, the lid being shaped to sealingly engage the mouth. An access aperture is located in the lid, the aperture being smaller in dimension than the mouth and being situated to one side of the lid. A separate cap is provided to engage the access aperture and seal the aperture. A collection spoon is secured to the underside of the lid and extends into the container, the spoon being located adjacent the aperture and being situated to a side of the lid which is generally opposite the side toward which the access aperture is located. The spoon has a scoop disposed at an angle relative to the vertical and being oriented toward the access aperture.

In accordance with the preferred form of the invention, the lid includes an attachment brace extending from the underside of the lid, and the spoon includes a shank shaped to engage and be secured to the brace. Thus, the lid and spoon form a unitary collection and sealing structure.

Preferably, the scoop of the spoon is disposed at an angle of approximately 45° to the vertical. This angular relationship is important, since if the angle were too steep, the lid would interfere with sample collection, while if the angle were to shallow, collection would be awkward, as would be depositing of a sample within the container. To facilitate sample collection, the spoon also includes a generally straight cutting edge.

Preferably, the access aperture is not fully at one side of the lid, but rather is located on a central raised ledge, with the spoon being secured to the underside of the ledge. The ledge is located centrally so that if the container is ever tipped when the cap is removed from the access aperture, the location of the aperture helps avoid spilling of any sample within the container.

BRIEF DESCRIPTION OF THE DRAWING

The invention is described in greater detail in the following description of an example embodying the best mode of the invention, taken in conjunction with the drawing figures, in which.

DESCRIPTION OF AN EXAMPLE EMBODYING THE INVENTION

Figure 1:
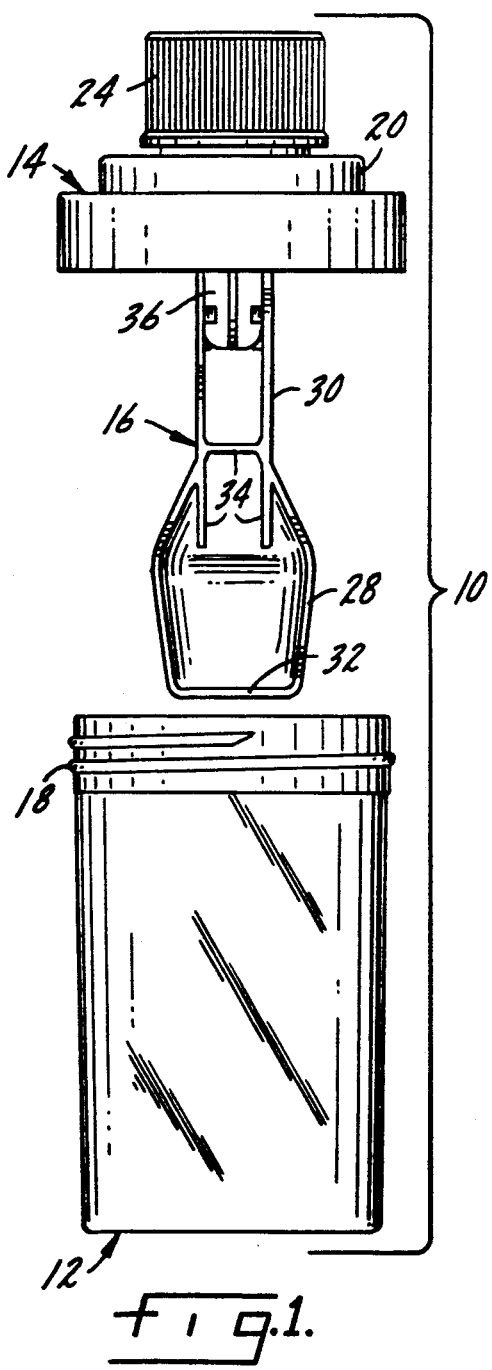
FIG. 1 is a front elevational assembly view of the stool collection and transport device according to the invention, with the lid removed from and positioned above the container.

A stool collection and transport device is shown generally at 10 in the drawing figures. It comprises as primary components an upright container 12, a removable lid 14, and a collection spoon 16 secured to the underside of the lid 14.

The lid 14 and container 12 sealingly mate with one another, and preferably the lid 14 and container 12 are threaded so that the lid 14 may be screw-applied to the container 12, threads 18 on the container 12 being shown in FIG. 1. A rotatable lid provides a positive seal between the lid 14 and the container 12 in case the container 12 is tipped. Also, rotating removal of the lid helps avoid contamination that might occur should the lid be snap applied to the container.

Figure 2:
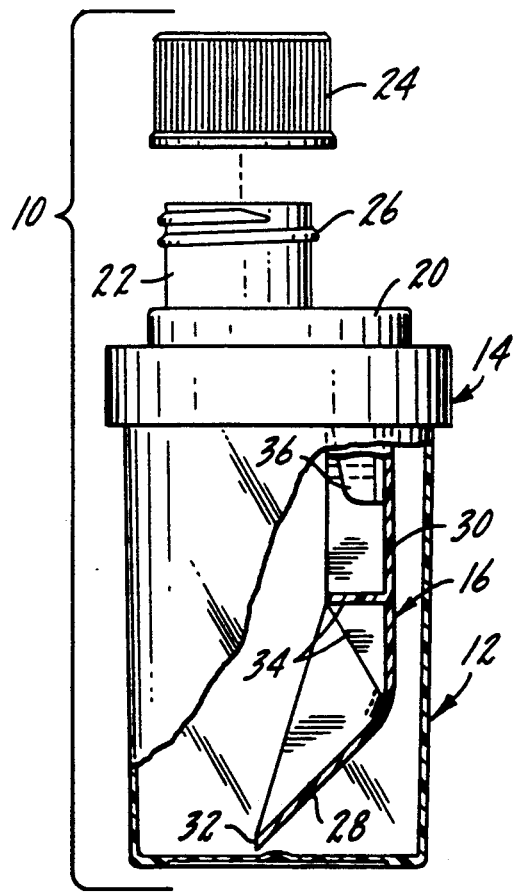
FIG. 2 is a side elevational view thereof, with the lid applied to the container, and with the cap removed from its spout, and with portions being in cross section to illustrate detail.
Figure 3:
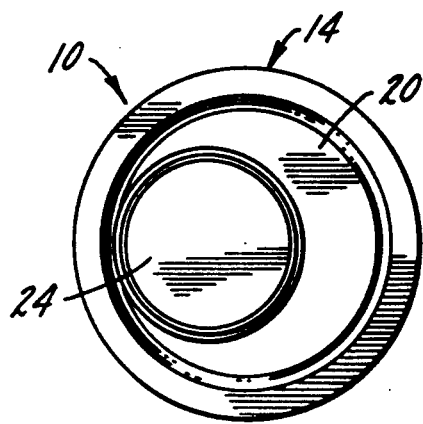
FIG. 3 is a top plan view of the stool collection and transport device.

The lid 14 includes a central, raised ledge 20 in which an access aperture is formed in the shape of an upstanding spout 22. A cap 24 is shaped to engage the spout 22 and seal the access aperture through the spout 22. Again, it is preferred that the cap and the spout 22 be threaded for application of the cap to the spout, threads 26 of the spout 22 being illustrated in FIG. 2.

The spoon 16 includes a scoop 28 extending from a generally vertical shank 30. The scoop 28 is disposed at an angle of approximately 45° to vertical to help avoid contamination of the user, and facilitate sample collection. The scoop 28 includes a generally straight bottom cutting edge 32. Ribs 34 are employed as necessary to strengthen the scoop 28 and the shank 30.

An attachment brace 36 is formed in the underside of the lid 14 beneath the raised ledge 20. The shank 30 and attachment brace 36 are shaped to mate as shown in the drawing figures, with the shank 30 being adhesively or otherwise secured to the brace 36 to permanently bond the spoon 16 to the underside of the lid 14.

ACHIEVEMENTS

The invention provides an extremely versatile and safe stool collection and transport device. With the lid 14 applied to the container 12, the spout 22 provides a secondary, restricted access to the interior of the container 12. The spout 22 is located to one side of the raised ledge 20, while the spoon 16 is secured to the underside of the raised ledge 20 at a side generally opposite to that where the spout 22 is located, thus positioning the spoon 16 adjacent one side of the container 12, and providing a relatively open area beneath the spout 22 for collection of samples through the access aperture created by the spout 22.

The ledge 20 is centrally located so that the spout 22 is not at an extreme edge of the lid 14. Location of the spout inwardly of the edge of the lid 14 helps prevent spilling if the device 10 is tipped while the cap 24 is removed.

The angle of the scoop 28 is important. Samples are normally collected by the user holding the lid 14 and positioning the scoop 28 for sample collection. With the scoop 28 angled at an angle of attack of approximately 45°, the user can readily collect a sample while holding the lid 14 without the lid 14 interfering or becoming contaminated by the sample. The angulation also allows for collection of samples whether liquid or solid, particularly facilitating collection of a liquid sample, again without interference of the lid 14. If the angle of attack of the scoop 28 were too steep relative to the vertical, the lid 14 would interfere with sample collection since the lid would tend to scrape any flat surface upon which the sample may lay, or would make entry into a collection bowl or pan extremely awkward or impossible. Were the angle too shallow, holding of the lid 14 for collection of a sample would be difficult, particularly if a sample is to be cut using the cutting edge 32. Also, were the angle of the scoop 28 too shallow, depositing of a sample within the container 12 would be more difficult, particularly when the sample is solid and clings to the scoop.

Location of the spoon 16 to one side of the lid 14, rather than in the center thereof, creates a relatively open area beneath the spout 22 for access to a sample when the cap 24 is removed while the lid 14 remains on the container 12. A separate stick, spatula or other object can be inserted through the spout 22 to collect part of the sample without removing the lid 14.

It is preferred that all elements of the stool collection and transport device 10 are molded from plastic, both for ease of fabrication and also disposability. The container 12 is preferably transparent, while other parts may or may not be, as desired. Four molded parts are necessary, the cap 24, the lid 14 including the spout 22 and the attachment brace 36, the spoon 16, and the container 12. After molding of the four parts, the only fabrication step (other than assembly of the parts), is attachment of the spoon 16 to the brace 36.

Various changes can be made to the invention without departing from the spirit thereof or scope of the following claims.

What is claimed is:

1. A stool collection and transport device comprising
   a. an upright container having means defining an open mouth at the top thereof,
   b. a removable lid for said container, said lid being shaped to sealingly engage said mouth,
   c. means defining an access aperture in said lid, said aperture being smaller in dimension than said mouth and being situated to one side of said lid,
   d. a cap shaped to engage said access aperture and seal said aperture, and
   e. a collection spoon secured to the underside of said lid and extending into said container, said spoon being located adjacent said aperture and being situated to a side of said lid generally opposite said one side, said spoon having a scoop disposed at an angle relative to vertical and being oriented toward said aperture.

2. A device according to claim 1 in which said lid includes an attachment brace extending from the underside of said lid, and said spoon includes a shank shaped to engage said brace and is secured thereto.

3. A device according to claim 1 in which said angle is approximately 45°.

4. A device according to claim 1 in which said spoon includes a generally straight cutting edge.

5. A device according to claim 4 in which said angle is approximately 45°.

6. A device according to claim 1 in which said lid includes a central raised ledge, said aperture being located in said ledge and said spoon being secured to the underside of said ledge.

* * * * *